United States Patent [19]

Muraishi et al.

[11] Patent Number: 4,855,109
[45] Date of Patent: Aug. 8, 1989

[54] CHEMICAL ANALYSIS APPARATUS

[75] Inventors: Katsuaki Muraishi, Kanagawa; Nakatsugu Yaginuma, Saitama; Kikuo Hirai, Saitama; Fuminori Arai, Saitama; Yuzo Iwata, Saitama, all of Japan

[73] Assignee: Fuji Photo Film Co., Ltd., Kanagawa, Japan

[21] Appl. No.: 12,693

[22] Filed: Feb. 9, 1987

[30] Foreign Application Priority Data

| Feb. 7, 1986 | [JP] | Japan | 61-25582 |
| Feb. 7, 1986 | [JP] | Japan | 61-25583 |
| Feb. 7, 1986 | [JP] | Japan | 61-25584 |
| Feb. 7, 1986 | [JP] | Japan | 61-25585 |
| Sep. 3, 1986 | [JP] | Japan | 61-207044 |
| Sep. 3, 1986 | [JP] | Japan | 61-207045 |

[51] Int. Cl.$^4$ .......................... B01N 35/04
[52] U.S. Cl. .................. 422/63; 422/65; 422/68; 436/43; 436/46
[58] Field of Search ................. 422/64–67, 422/68, 63; 436/43–44, 46–48

[56] References Cited

U.S. PATENT DOCUMENTS

| 4,224,032 | 9/1980 | Glover et al. | 422/65 X |
| 4,250,266 | 2/1981 | Wade | 422/67 X |
| 4,302,420 | 11/1981 | Jakubowicz et al. | 422/65 X |
| 4,303,611 | 12/1981 | Jessop | 422/65 |
| 4,584,275 | 4/1986 | Okano et al. | 436/46 X |
| 4,647,431 | 3/1987 | Sekine et al. | 436/46 X |

FOREIGN PATENT DOCUMENTS

| 3230901 | 3/1983 | Fed. Rep. of Germany. |
| 53-21677 | 7/1978 | Japan. |
| 55-164356 | 12/1980 | Japan. |
| 56-77746 | 6/1981 | Japan. |
| 58-21566 | 2/1983 | Japan. |

Primary Examiner—Michael S. Marcus
Assistant Examiner—Jill Johnston
Attorney, Agent, or Firm—Sughrue, Mion, Zinn, Macpeak & Seas

[57] ABSTRACT

A chemical analysis apparatus comprises a slide loading section for holding chemical analysis slides, a section for applying a sample material to the chemical analysis slide, and an incubator provided with housing compartments for housing the chemical analysis slides side by side in a transverse direction on the same plane. The apparatus also comprises a read-out head slideable in the transverse direction and disposed to face the chemical analysis slide housed in the housing compartment via a readout opening formed in each housing compartment, thereby emitting light to the chemical analysis slide and measuring the reflection optical density thereof. A conveyance and feed-in system is disposed for conveying the chemical analysis slide held at the slide loading section to the sample applying section, conveyig the chemical analysis slide having a reagent layer with the sample material applied thereon to a position facing an inlet opening of the housing compartment, and then feeding the chemical analysis slide into the housing compartment from the inlet opening thereof.

9 Claims, 9 Drawing Sheets

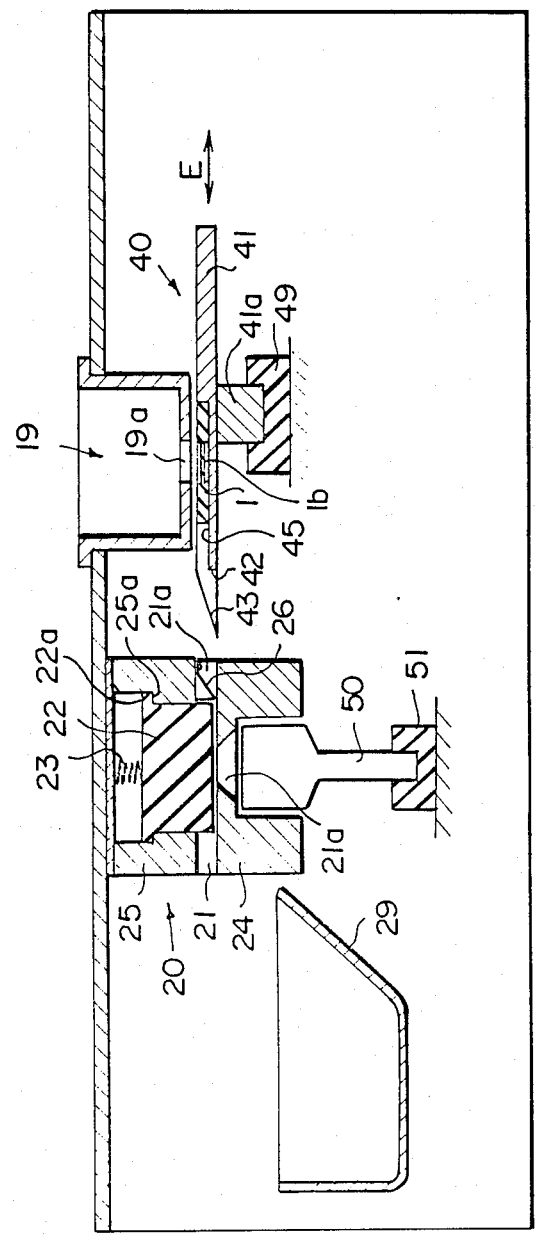

F I G. 6B
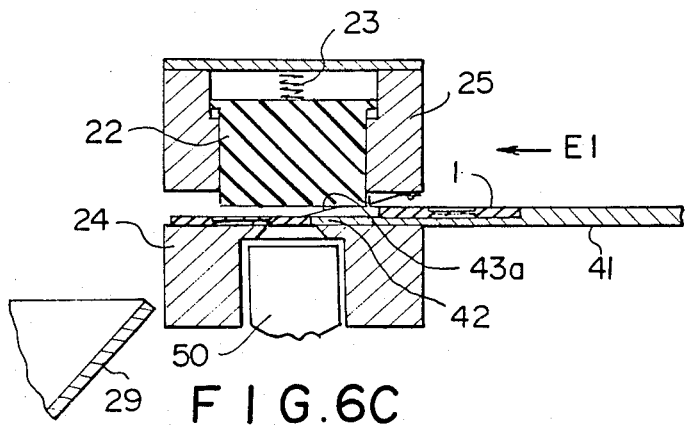
F I G. 6C
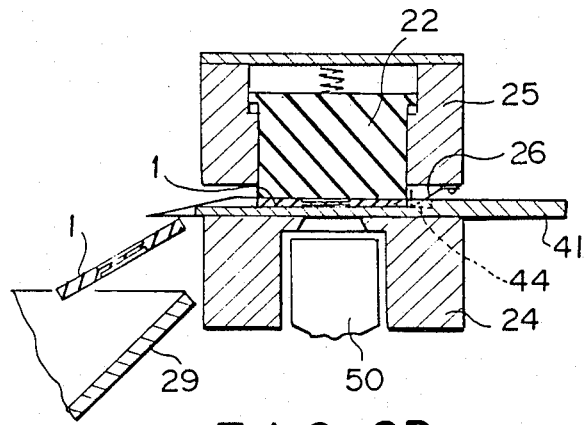
F I G. 6D
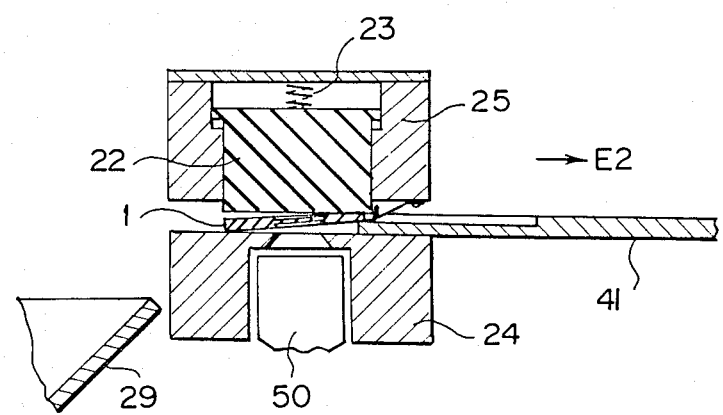

CHEMICAL ANALYSIS APPARATUS

BACKGROUND OF THE INVENTION

1. Field of the Invention

This invention relates to a chemical analysis apparatus for applying a sample material to a chemical analysis slide, i.e. a slide type chemical analysis device, provided with a single reagent layer or a plurality of reagent layers, maintaining the chemical analysis slide at a predetermined temperature (i.e. conducting incubation) for a predetermined time, and then optically measuring the degree of color formation in the chemical analysis slide for analysis of the sample material.

2. Description of the Prior Art

Qualitative or quantitative analysis of a specific chemical constituent in a liquid sample is generally conducted for various industrial purposes Particularly, it is very important in biochemical and clinical categories to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a sample solution simply by applying a droplet of the sample solution With the chemical analysis slide, it is possible to analyze a sample solution more simply and more quickly than when the conventional wet type analysis method is used. Therefore, the use of the chemical analysis slide is desirable particularly in medical organizations, research laboratories, or the like where many samples are to be analyzed.

In order to analyze a chemical constituent or the like contained in a sample solution by use of the chemical analysis slide, a measured amount of the sample solution is put on the chemical analysis slide and is maintained at a predetermined temperature (i.e. incubated) for a predetermined time in an incubator to cause a color reaction, and the reflection optical density is measured by exposing the chemical analysis slide to measuring light having a wavelength selected in advance in accordance with the combination of the constituent of the sample solution with a reagent contained in the reagent layer of the chemical analysis slide. In this manner, it is possible to achieve quantitative analysis of the chemical constituent or the like.

In the medical organizations, research laboratories or the like, since many samples are to be analyzed, it is desirable that the analysis be conducted automatically and continuously. To satisfy this need, there have been proposed various chemical analysis apparatuses for carrying out sample analysis automatically and continuously by use of the aforesaid chemical analysis slides.

For example, it has been proposed in Japanese Unexamined Patent Publication No. 56(1981)-77746 to constitute a chemical analysis apparatus so that chemical analysis slides are disposed in an equally spaced relation to each other in the circumferential direction between two rotatable disks provided with an incubation heater for conducting incubation by the heater, the chemical analysis slide incubated for a predetermined time is positioned by rotation of the disks to face a read-out head disposed below the disks, and exposure of the chemical analysis slide to measuring light and measurement of reflection optical density are conducted by the read-out head via an opening in the bottom surface of the disk. With the proposed chemical analysis apparatus, it is possible to dispose a plurality of the chemical analysis slides in the circumferential direction between the two disks, and therefore to conduct analysis efficiently and quickly. However, the proposed chemical analysis apparatus has the drawbacks that the configurations of the disk rotation system and the control system for controlling the disk rotation system become complicated and the chemical analysis apparatus cannot be made very small and cheaply.

Also, as disclosed in Japanese Unexamined Patent Publication No. 58(1983)-21566, there has been proposed a chemical analysis apparatus wherein a conveyance path in a U-shaped form or the like is formed in an incubator, a plurality of chemical analysis slides supported by a carrier having a predetermined shape are sequentially fed into the conveyance path and conveyed along the conveyance path, and exposure of the chemical analysis slide, which has been incubated for a predetermined time in the conveyance path, to measuring light and measurement of reflection optical density are conducted by a read-out head disposed midway of the conveyance path. Also with the proposed chemical analysis apparatus, it is possible to conduct analysis efficiently and quickly by use of a plurality of the chemical analysis slides. However, since it is necessary to provide the mechanism for conveying the carriers supporting the chemical analysis slides along the conveyance path, the proposed chemical analysis apparatus is not completely suitable for making the apparatus small and decreasing the cost. Further, the proposed chemical analysis apparatus is not easily adaptable for measurement of the change rate of the reflection optical density conducted by measuring the reflection optical density of the same chemical analysis slide many times at predetermined time intervals.

In a different example of the chemical analysis apparatus, chemical analysis slides are sequentially fed and stacked in an incubator. After a predetermined time has elapsed, the stacked chemical analysis slides are sequentially fed out starting with the lowest slide and subjected to measurement of the reflection optical density. With this configuration, since the chemical analysis slides are stacked in the incubator, it is easy to conduct incubation and the incubator may be made small. However, the chemical analysis apparatus has the drawback that gas generated by the color reaction between a reagent of the chemical analysis slide with a sample applied to the chemical analysis slide while the chemical analysis slide is being incubated adversely affects the color reactions in the other chemical analysis slides, and the analysis accuracy becomes low. Also, with the chemical analysis apparatus, since the chemical analysis slides are sequentially fed out and subjected to the measurement after a predetermined time has elapsed, it is not always possible to conduct the measurement midway during the incubation. Therefore, the chemical analysis apparatus is not suitable for the measurement of the change rate of the reflection optical density.

SUMMARY OF THE INVENTION

The primary object of the present invention is to provide a chemical analysis apparatus which is comparatively small and compact and has a simple configuration, and which conducts chemical analysis quickly and accurately.

Another object of the present invention is to provide a chemical analysis apparatus which is comparatively small and compact and has a simple configuration, which conducts chemical analysis quickly and accurately, and wherein measurement of fog of a chemical analysis slide and measurement of reflection optical density after a color reaction are conducted with a single read-out head.

A further object of the present invention is to provide a chemical analysis apparatus which is provided with a plurality of incubators, which is comparatively small and compact and has a simple configuration, and which conducts chemical analysis quickly and accurately.

The specific object of the present invention is to provide a chemical analysis apparatus which is provided with an incubator for securing and supporting a chemical analysis slide in a housing compartment and a feed-in and ejection means for feeding the chemical analysis slide into and out of the housing compartment, which is comparatively small and compact and has a simple configuration, and which conducts chemical analysis quickly and accurately.

The present invention provides a chemical analysis apparatus comprising:

(i) a slide loading section for holding at least one chemical analysis slide, (ii) a sample applying section for applying a predetermined amount of a sample material on said chemical analysis slide, (iii) an incubator provided with a plurality of housing compartments for housing a plurality of the chemical analysis slides in the form placed side by side in a transverse direction on the same plane, (iv) a read-out head slideable in said transverse direction and disposed for standing face to face with said chemical analysis slide housed in one of said plurality of the housing compartments via a read-out opening formed in each of said housing compartments, thereby emitting light to said chemical analysis slide and measuring reflection optical density of said chemical analysis slide, and (v) a conveyance and feed-in means for conveying said chemical analysis slide held at said slide loading section to said sample applying section, conveying said chemical analysis slide having a reagent layer with said sample material applied thereon to a position facing an inlet opening of one of said housing compartments, and then feeding said chemical analysis slide into said housing compartment from the inlet opening thereof.

The present invention also provides a chemical analysis apparatus as mentioned above, wherein a fog measuring section for measuring the reflection optical density of said chemical analysis slide before said sample material is applied to said chemical analysis slide is disposed on the lateral side of said incubator in said transverse direction, said read-out head is slideable in said transverse direction to face said fog measuring section, and said chemical analysis slide conveyed by said conveyance and feed-in means from said slide loading section to said sample applying section is made to pass through said fog measuring section, whereby fog measurement is conducted by said read-out head at said fog measuring section.

The present invention further provides a chemical analysis apparatus comprising:

(i) a sample applying section for applying a predetermined amount of a sample material to a reagent layer of a chemical analysis slide provided with at least one reagent layer, (ii) a first incubator provided with a plurality of first housing compartments for housing a plurality of the chemical analysis slides in the form placed side by side in a transverse direction on the same plane, (iii) a second incubator disposed on the lateral side of said first incubator in said transverse direction and provided with at least one second housing compartment for housing at least one chemical analysis slide and standing side by side with said first housing compartment in said transverse direction on the same plane as said first housing compartment, (iv) a read-out head slideable in said transverse direction and disposed for standing face to face with said reagent layer of said chemical analysis slide housed in one of said first housing compartments via a read-out opening formed in each of said first housing compartments, thereby emitting light to said reagent layer and measuring reflection optical density of said reagent layer, and (v) a conveyance and feed-in means disposed slideably in said transverse direction to face inlet openings of said first housing compartments and said second housing compartment for conveying said chemical analysis slides one by one to said sample applying section, conveying said chemical analysis slide having said reagent layer with said sample material applied thereon to a position facing the inlet opening of one of said first housing compartments or the inlet opening of said second housing compartment, and then feeding said chemical analysis slide into said first housing compartment or said second housing compartment from the inlet opening thereof.

The present invention still further provides a chemical analysis apparatus comprising:

(i) an incubator provided with a housing compartment for housing a chemical analysis slide having a reagent layer with a sample material applied thereon and maintaining said chemical analysis slide at a predetermined temperature, (ii) a read-out head for facing said reagent layer of said chemical analysis slide housed in said housing compartment via a read-out opening formed in said housing compartment, emitting light to said reagent layer, and measuring reflection optical density of said reagent layer, and (iii) a slide feed-in and ejection means for ejecting said chemical analysis slide housed in said housing compartment out of said housing compartment and feeding a new chemical analysis slide into said housing compartment, wherein said housing compartment of said incubator is provided with a supporting member for supporting one surface of said chemical analysis slide and having said readout opening, and a pushing member contacting the other surface of said chemical analysis slide and urged toward said one surface of said chemical analysis slide, thereby grasping said chemical analysis slide between said pushing member and said supporting member, said housing compartment has an inlet opening provided with a stopper member for allowing said chemical analysis slide to enter said housing compartment from said inlet opening and preventing said chemical analysis slide in said housing compartment from coming out of said housing compartment, and said slide feed-in and ejection means comprises:

(a) a holding portion capable of being inserted into said housing compartment and supporting said new chemical analysis slide thereon, (b) a wedge-like insert portion disposed at a front end of said holding portion on the lateral side of said holding portion for releasing the grasping of said chemical analysis slide by said pushing member when said wedge-like insert portion is inserted into said housing compartment, (c) a slide ejecting protrusion disposed on the front side of said holding portion for contacting the rear end of said chemical analysis slide released by said wedge-like insert portion from grasping when said slide ejecting protrusion is inserted into said housing compartment and pushing said chemical analysis slide toward an outlet opening disposed on the side opposite to said inlet opening, thereby ejecting said chemical analysis slide, and (d) an engagement means for making said new chemical analysis slide engage with said stopper member when said new chemical analysis slide supported on said holding portion is positioned inside of said housing compartment.

With the first and second mentioned chemical analysis apparatuses in accordance with the present invention, since the slide loading section, the sample applying section, the incubator and the read-out head are built in a single apparatus and the chemical analysis slide is automatically conveyed among said sections by the conveyance and feed-in means, it is possible to make the apparatus comparatively small and compact, to simplify the apparatus configuration, and to achieve automatic and continuous chemical analysis quickly and accurately. Also, with the second mentioned chemical analysis apparatus in accordance with the present invention, since the fog measuring section is provided for measuring fog of the chemical analysis slide by moving the read-out head to the lateral side of the incubator in the transverse direction and the chemical analysis slide conveyed by the conveyance and feed-in means from the slide loading section to the sample applying section is made to pass through the fog measuring section to conduct fog measurement, it is possible to conduct fog measurement and measurement of the reflection optical density after a color reaction with a single read-out head.

With the third mentioned chemical analysis apparatus in accordance with the present invention, the first incubator and the second incubator are disposed side by side in the transverse direction, the housing compartments of the first and second incubators are disposed side by side in the transverse direction on the same plane, and the chemical analysis slide having the reagent layer with the sample material applied thereon is fed into a predetermined housing compartment by the conveyance and feed-in means slideable in the transverse direction to face the inlet opening of each housing compartment. Therefore, it is possible to maintain the chemical analysis slides at different temperatures in the respective incubators and to conduct different measurements. Also, since it is only necessary that a single conveyance and feed-in means be provided, it is possible to make the apparatus small and compact.

With the fourth mentioned chemical analysis apparatus in accordance with the present invention, the housing compartment of the incubator for housing the chemical analysis slide and effecting incubation and measurement of optical density by the read-out head is composed of the supporting member having the read-out opening, the pushing member for holding the chemical analysis slide against the supporting member, and the stopper member for preventing the chemical analysis slide from coming out of the housing compartment. In the course of feeding of the chemical analysis slide into the housing compartment and ejection of the chemical analysis slide therefrom by the slide feed-in and ejection means, grasping of the chemical analysis slide by the pushing member is released by the wedge-like insert portion, and then the chemical analysis slide is ejected from the housing compartment by the slide ejecting protrusion. Also, a new chemical analysis slide held on the holding portion is disposed at a predetermined position in the housing compartment, and then the slide feed-in and ejection means alone is returned from the housing compartment with the chemical analysis slide maintained at the predetermined position by the stopper member. Therefore, it is possible to secure and hold the chemical analysis slide in the housing compartment, and to maintain a high accuracy of the measurement of reflection optical density conducted by the read-out head by maintaining the distance between the chemical analysis slide and the read-out head at a predetermined value. Also, it is possible to automatically conduct ejection of the chemical analysis slide from the housing compartment after the measurement is finished and feeding of a new chemical analysis slide into the housing compartment. It is also possible to conduct feed-in and ejection of the chemical analysis slide simultaneously or independently.

BRIEF DESCRIPTION OF THE DRAWINGS

FIG. 4A is a sectional view taken along line V—V of FIG. 2.

DESCRIPTION OF THE PREFERRED EMBODIMENTS

The present invention will hereinbelow be described in further detail with reference to the accompanying drawings.

Figure 1:
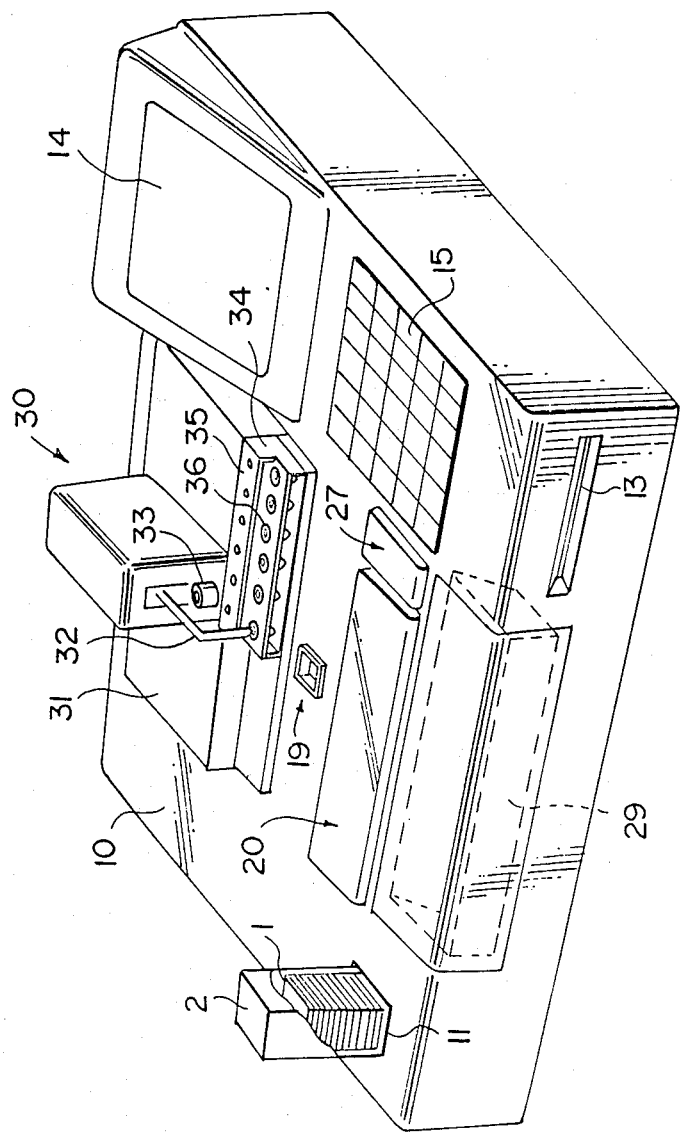
FIG. 1 is a perspective view showing an embodiment of the chemical analysis apparatus in accordance with the present invention.
Figure 2:
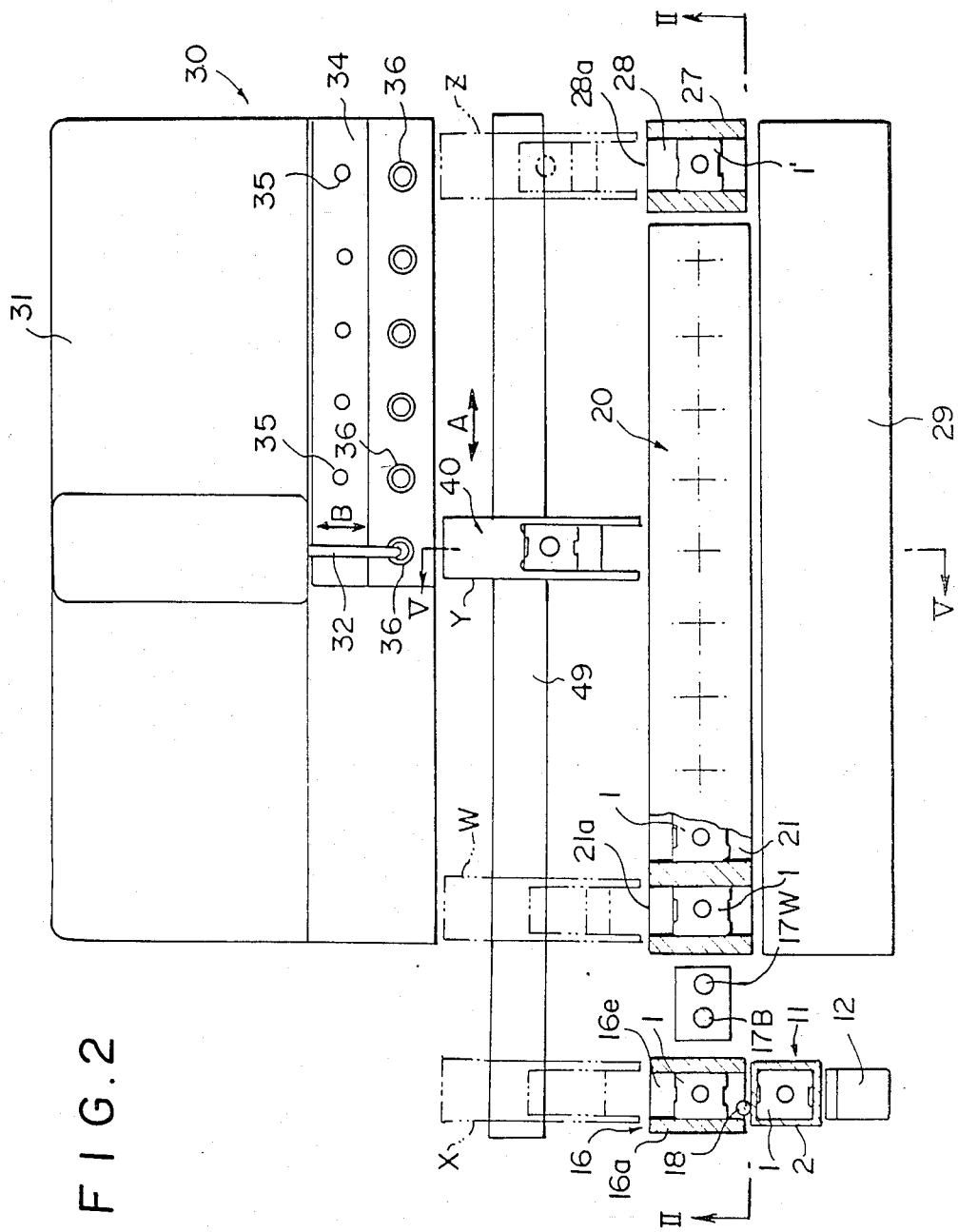
FIG. 2 is a plan view showing the embodiment of FIG. 1.
Figure 3:
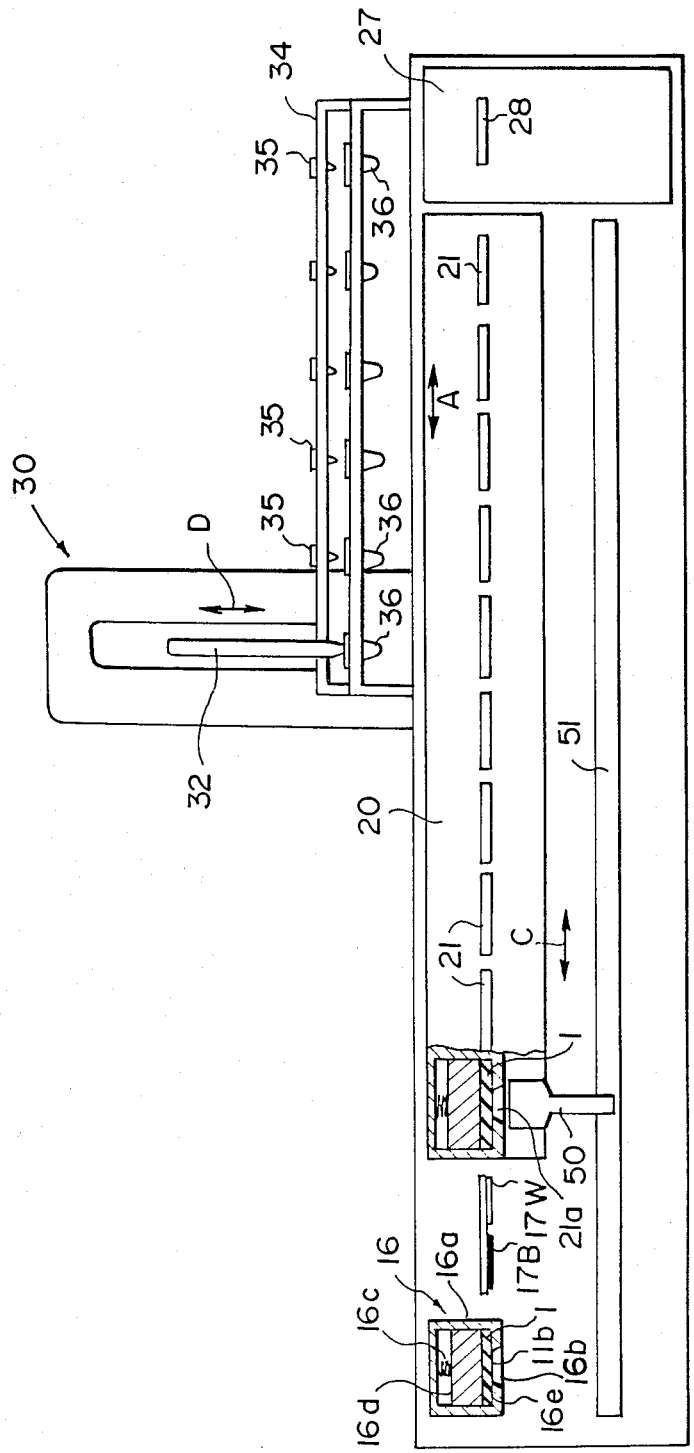
FIG. 3 is a front view taken along lien II—II of FIG. 2.

Referring to FIG. 1, a cartridge loading section 11, a first incubator 20, a second incubator 27, a sample applying device 30, and a conveyance and feed-in means 40 are provided on a main body 10. FIG. 2 is a plan view of FIG. 1, and FIG. 3 is a front view taken along line II—II of FIG. 2. This embodiment is also provided with a display section 14 for displaying the measured values in the course of measurement or the like, operating key section 15 for controlling the displaying of the measured values or the like, and a magnetic disk inserting section 13 for recording the measured values or the like on a magnetic disk, which are omitted for simplicity of explanation in FIGS. 2 and 3.

Figure 5:
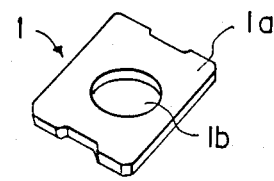
FIG. 5 is a perspective view showing an example of the chemical analysis slide used in the embodiment of FIG. 1, FIGS. 6A, 6B, 6C and 6D are sectional views showing the operation of feeding the chemical analysis slide into the housing compartment of the incubator by the conveyance and feed-in means.
Figure 6A:
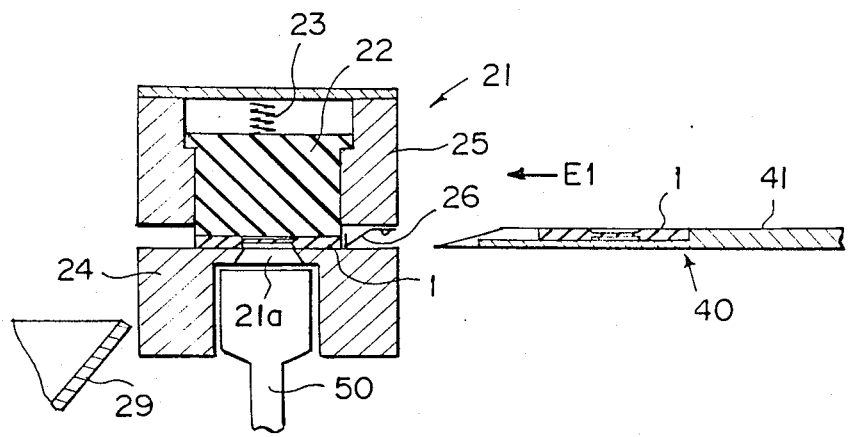

A cartridge 2 houses a plurality of unused chemical analysis slides 1, 1, ... stacked one upon another. As shown in FIG. 5, each of the chemical analysis slides 1, 1, ... loaded to the loading section 11 comprises a frame 1a having a circular hole for applying a liquid sample, and a dry type multi-layer film 1b disposed in the frame 1a and composed of a supporting material, a reagent layer, and a development layer, which are stacked in this sequence. A predetermined amount of the sample material such as urine or blood is fed onto the film 1b, and incubated to cause a color reaction. The chemical analysis slides 1, 1, ... in the cartridge 2 are pushed out by a pushing lever 12 one by one, starting from the lowest chemical analysis slide 1, to the fog measuring section 16. The fog measuring section 16 measures the reflection density (fog density) of the film 1b of the chemical analysis slide 1 before the chemical analysis slide 1 is provided with the sample material, and the measured fog density value is used for judging whether the chemical analysis slide 1 is acceptable or not and for correcting the measured density value of the chemical analysis slide 1, which is obtained after a color reaction, in accordance with the fog density. The fog measuring section 16 is composed of a frame 16a provided with a measuring opening 16b at the lower section, and a retaining member 16d urged by a spring 16c in the frame 16a, and a housing compartment 16e for housing the chemical analysis slide 1 is formed between the lower inner surface of the frame 16a and the retaining member 16d. A bar code reading means 18 for reading a bar code (not shown) indicated on the chemical analysis slide 1 is disposed on the slide insertion side of the housing compartment 16e. A white reference plate 17W and a black reference plate 17B for eliminating error in the measured reflection density value of the chemical analysis slide 1 are disposed on the rightward lateral side of the fog measuring section 16. Also, the first incubator 20 is disposed on the rightward lateral side of the white reference plate 17W and the black reference plate 17B. A plurality of housing compartments 21, 21, ... for housing the chemical analysis slides 1, 1, ... are formed in the first incubator 20 so that the chemical analysis slides 1, 1, ... stand side by side on the same plane as the chemical analysis slide 1 in the fog measuring section 16. A receiving member 29 for receiving the used chemical analysis slides 1, 1, ... ejected from the housing compartments 21, 21, ... is disposed in front of the first incubator 20. Further, as shown in FIG. 3, a read-out head 50 slideable in the transverse direction as indicated by the arrow C to face the lower surface of the first incubator 20 is disposed below the first incubator 20. The read-out head 50 is slid on a rail 51 extending in the transverse direction below the first incubator 20 by being operated by, for example, a linear motor. The rail 51 extends up to the position below the fog measuring section 16, and therefore the read-out head 50 can be slid up to the fog measuring section 16 to face the chemical analysis slide 1 at the fog measuring section 16.

The first incubator 20 incorporates a heater (not shown) for incubating the chemical analysis slides 1, 1, ... in the housing compartments 21, 21, ....

The second incubator 27 is disposed on the rightward lateral side of the first incubator 20 and provided with a housing compartment 28 for housing a chemical analysis slide 1'. The housing compartment 28 is placed side by side with the housing compartments 21, 21, ... of the first incubator 20 in the transverse direction on the same plane as the housing compartments 21, 21, .... The first incubator 20 and the second incubator 27 are secured to the main body 10. Since the first incubator 20 and the second incubator 27 are disposed independently of each other, it is possible to maintain the chemical analysis slides at different temperatures.

The fog measuring section 16 and the first incubator 20 are thermally insulated from each other, and the first incubator 20 and the second incubator 27 are thermally insulated from each other.

In this embodiment, the chemical analysis slide 1 housed in the first incubator 20 is subjected to a color reaction between the sample material applied to the film of the chemical analysis slide 1 and the reagent of the film, and the extent of the color reaction is optically measured by the read-out head 50 via a read-out opening 21a formed in the lower surface of the housing compartment 21. On the other hand, the chemical analysis slide 1' (electrolyte slide) housed in the second incubator 27 is used for measuring the ionic activity of a specific ion contained in the sample material by measuring a difference in potential generated in proportion to the logarithm of the ionic activity of the specific ion. Therefore, the chemical analysis slide 1' housed in the second incubator 27 is basically composed of at least one pair of solid electrodes having an ion selective layer as the outermost layer, and a porous bridge exhibiting capillary action disposed between the pair of the ion selective layers of the solid electrodes. A reference solution is applied to an ion selective layer of the solid electrode pair of the chemical analysis slide 1', and a sample solution (sample material) is applied to the other ion selective layer. A difference in potential generated between the electrodes is measured by electrode heads mounted on the lower surface of the second incubator 27, thereby measuring the ionic activity of a specific ion in the sample solution. At the first incubator 20, in order to cause the color reaction of the sample such as urine or blood, it is necessary to maintain the chemical analysis slides 1, 1, ... at a temperature approximately equal to the body temperature (37° C.). However, at the second incubator 27, the temperature need not be maintained at this level, and may be maintained at, for example, approximately 30° C. This embodiment is advantageous in such a case since the first incubator 20 and the second incubator 27 are disposed independently of each other.

On the other hand, the conveyance and feed-in means 40 slideable in the transverse direction as indicated by the arrow A to face one of inlet openings 21a, 21a, ... of the housing compartments 21, 21, ... and an inlet opening 28a of the housing compartment 28 is disposed at the rear of the first incubator 20 and the second incubator 27. The conveyance and feed-in means 40 is mounted on a rail 49 extending in the transverse direction and made to slide by a linear motor or the like. The conveyance and feed-in means 40 is slideable up to a position facing the fog measuring section 16 (the position as indicated by the chain line X in FIG. 2) besides the positions facing the first incubator 20 and the second incubator 27. Therefore, the chemical analysis slide 1 or 1' pushed by the pushing lever 12 out of the fog measuring section 16 can be received by the conveyance and feed-in means 40 sliding to the position as indicated by the chain line X.

The sample applying device 30 is disposed at the rear of the conveyance and feed-in means 40. The sample applying device 30 is slideable in the transverse direction as indicated by the arrow A on a base plate 31, and provided with a sample base 34 on which sample tubes 36, 36, ... and application tips 35, 35, ... are disposed in two lines in the transverse direction. A pipette 32 moveable vertically as indicated by the arrow D and forwardly and backwardly as indicated by the arrow B with respect to the base plate 31 moves vertically, forwardly and backwardly to fit one of the application tips 35, 35, ... to the lower end of the pipette 32, to draw a predetermined amount of the sample material contained in one of the sample tubes 36, 36, ... by suction, and then to feed a spot of the sample material onto the film 1b of the chemical analysis slide 1 on the conveyance and feed-in means 40 at a sample applying section 19. At this time, the application tips 35, 35, ... are exchanged for the respective sample tubes 36, 36, ... so that the sample materials contained in the sample tubes 36, 36, ... are not mixed with each other. In the case of the chemical analysis slide 1', since application of a reference solution is also necessary, the reference solution is drawn from a reference solution cup 33 as shown in FIG. 1 and then applied.

The chemical analysis slide 1 or 1' with the sample material applied thereon is fed by the conveyance and feed-in means 40 into the predetermined housing compartment. The configurations of the conveyance and feed-in means 40 and the first incubator 20 will hereinbelow be described with reference to FIG. 4A which is a sectional view taken along line V—V of FIG. 2.

Figure 4B:
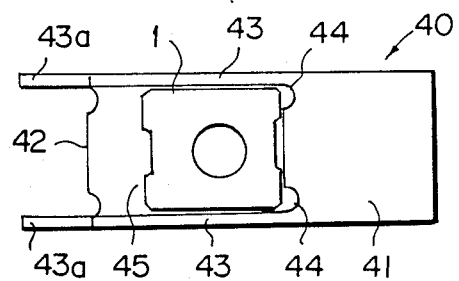
FIG. 4B is a plan view showing the conveyance and feed-in means in the embodiment of FIG. 1.

The conveyance and feed-in means 40 is disposed below a cover plate and is composed of a supporting block 41a slideable in the transverse direction as indicated by the arrow A along the rail 49, and a supporting plate 41 disposed on the supporting block 41a. FIG. 4B is a plan view of the conveyance and feed-in means 40. The supporting plate 41 is constituted by a holding portion 45 for supporting the chemical analysis slide 1 thereon, step-like portions 43, 43 formed at both ends of the holding portion 45, a pair of wedge-like insert portions 43a, 43a which are pointed forwardly and formed at the leading ends of the step-like portions 43, 43, a slide ejecting protrusion 42 formed at the leading end of the holding portion 45, and a pair of recesses 44, 44 formed rearwardly of both side portions of the rear end face of the chemical analysis slide 1 held at the holding portion 45. When the conveyance and feed-in means 40 is moved in the transverse direction along the rail 49 up to the position as indicated in FIG. 4A, the film 1b of the chemical analysis slide 1 held at the holding section 45 stands facing an opening 19a of the sample applying section 19, and the sample material is applied from the pipette 32 of the sample applying device 30 onto the film 1b via the opening 19a. Then, the conveyance and feed-in means 40 is moved along the rail 49 up to the position facing the housing compartment 21 or 28 which is to house the chemical analysis slide 1. The supporting plate 41 is slideable on the supporting block 41a forwardly and backwardly as indicated by the arrow E, and the chemical analysis slide 1 held on the supporting plate 41 is fed into the housing compartment 21 of the first incubator 20 or the housing compartment 28 of the second incubator 27 by the sliding of the supporting plate 41.

The first incubator 20 is composed of a supporting member 24 for supporting the chemical analysis slide 1 fed into the first incubator 20 and having a read-out opening 21a, a pushing member 22 facing the supporting member 24 and moveable vertically, a spring 23 for urging the pushing member 22 downwardly, a main body member 25 for moveably supporting the pushing member 22, and a stopper leaf spring 26 secured to the inlet opening 21a of the housing compartment 21. Feeding of the chemical analysis slide 1 into the housing compartment 21 conducted by the conveyance and feed-in means 40 will be described hereinbelow with reference to FIGS. 6A, 6B, 6C and 6D.

The case wherein the chemical analysis slide 1 on which read-out by the read-out head 50 via the read-out opening 21a has been finished is housed and held in the housing compartment 21 and is to be replaced by a new chemical analysis slide 1 on the conveyance and feed-in means 40 will be described below. The chemical analysis slide 1 in the housing compartment 21 is grasped between the supporting member 24 and the pushing member 22 by the urging force of the spring 23. Therefore, when the supporting plate 41 is moved forwardly as indicated by the arrow E1, the wedge-like insert portion 43a first enters between the pushing member 22 and the supporting member 24, and pushes the pushing member 22 up to release grasping of the chemical analysis slide 1 as shown in FIG. 6B. Then, the slide ejecting protrusion 42 comes into contact with the rear end of the chemical analysis slide 1 in the housing compartment 21, pushes the chemical analysis slide 1 forwardly in the direction as indicated by the arrow E1, and ultimately ejects the chemical analysis slide 1 out of the housing compartment 21 into the receiving member 29 as shown in FIG. 6C. At this time, the new chemical analysis slide 1 held at the holding portion 45 of the supporting plate 41 is disposed at a predetermined position in the housing compartment 21, and the stopper leaf spring 26 enters the recesses 44, 44 formed rearwardly of the both side portions of the rear end face of the chemical analysis slide 1. The leaf spring 26 is forked into two branches or split into two portions to fit into the recesses 44, 44. Thereafter, the supporting plate 41 is returned backwardly as indicated by the arrow E2. At this time, since the stopper leaf spring 26 contacts the rear end face of the chemical analysis slide 1 and prevents the chemical analysis slide 1 from moving, the supporting plate 41 alone is returned backwardly and, as a result, the chemical analysis slide 1 is grasped between the supporting member 24 and the pushing member 22 in the housing compartment 21.

The conveyance and feed-in means 40 should preferably be preheated by a heater or the like for preventing the temperature of the first incubator 20 from changing (heat shock) when the supporting plate 41 is inserted into the housing compartment 21 of the first incubator 20.

In the case where the aforesaid conveyance and feeding means 40 is used, the operation of inserting a new chemical analysis slide 1 into the housing compartment 21 when no chemical analysis slide 1 is present in the housing compartment 21 or the operation of ejecting the chemical analysis slide 1 out of the housing compartment 21 can be conducted independently by the aforesaid operation of the supporting plate 41.

The operations of the aforesaid embodiment will be described hereinbelow.

First, the lowest chemical analysis slide 1 among the chemical analysis slides 1, 1, ... stacked in the cartridge 2 loaded to the cartridge loading section 11 is pushed out by the pushing lever 12, and housed in the housing compartment 16e at the fog measuring section 16. At this time, the bar code of the chemical analysis slide 1 is read by the bar code reading means 18. Thereafter, the read-out head 50 is moved to the position facing the measurement opening 16b of the fog measuring section 16, and fog measurement is conducted on the chemical analysis slide 1 before it is provided with the sample material. When the read-out head 50 is moved, it stands facing the white reference plate 17W and the black reference plate 17B, and photometric error is eliminated. After the fog measurement is conducted, the chemical analysis slide 1 is pushed by the pushing lever 12 onto the holding portion 45 of the conveyance and feed-in means 40 moved to the position as indicated by the chain line in FIG. 2.

In the case where the chemical analysis slide is found to be the electrolyte slide 1' by bar code reading, the fog measurement is not conducted, and the chemical analysis slide 1' is directly pushed by the pushing lever 12 onto the holding portion 45 of the conveyance and feed-in means 40.

Then, the conveyance and feed-in means 40 is moved rightwardly along the rail 49 up to the position as indicated by the solid line Y in FIG. 2 facing the pipette 32 of the sample applying device 30. The pipette 32 is moved vertically, forwardly and backwardly to fit the application tip 35 to the lower end of the pipette 32, and draws a predetermined amount of the sample material contained in the sample tube 36 into the application tip 35. The sample material is then fed onto the film 1b of the chemical analysis slide 1 or the chemical analysis slide 1' held on the conveyance and feed-in means 40.

Thereafter, the conveyance and feed-in means 40 is moved along the rail 49 in the transverse direction as indicated by the arrow A to the position facing the predetermined housing compartment 21 of the first incubator 20 or the housing compartment 28 of the second incubator 27 in accordance with the code read by the bar code reading means 16. As mentioned above, the chemical analysis slide 1 or 1' is fed into the housing compartment 21 or 28 by the operations as shown in FIGS. 6A, 6B, 6C and 6D. For the chemical analysis slide 1 incubated in the first incubator 20, emission of light and measurement of the reflection optical density are conducted via the read-out opening 21a by the read-out head 50 moved to the position below the housing compartment 21. On the other hand, at the second incubator 27, the difference in potential between the electrodes of the chemical analysis slide 1' is measured. When the measurement is finished, the chemical analysis slide 1 or the chemical analysis slide 1' is ejected from the housing compartment 21 or the housing compartment 28 into the receiving member 29 by the conveyance and feed-in means 40. It is possible to conduct chemical analysis automatically and continuously by using many chemical analysis slides and repeating the aforesaid operations.

In the aforesaid embodiment, though the measurement of the electrolyte slide is conducted at the second incubator 27, measurement of any other item may be conducted at the second incubator 27. In the case where measurement of the reflection optical density is to be conducted at the second incubator 27 like the first incubator 20, the read-out head 50 may be constituted to slide up to the position facing the second incubator 27 for conducting measurement. Also, the number of the housing compartments of the second incubator 27 is not limited to one, and a plurality of the housing compartments may be disposed at the second incubator 27. Further, instead of automatically applying the sample material by the sample applying device 30 at the sample applying section 19, the sample material may be manually applied by use of a micropipette or the like at the sample applying section 19.

Another embodiment of the chemical analysis apparatus in accordance with the present invention will hereinbelow be described with reference to FIGS. 7, 8 and 9.

Figure 7:
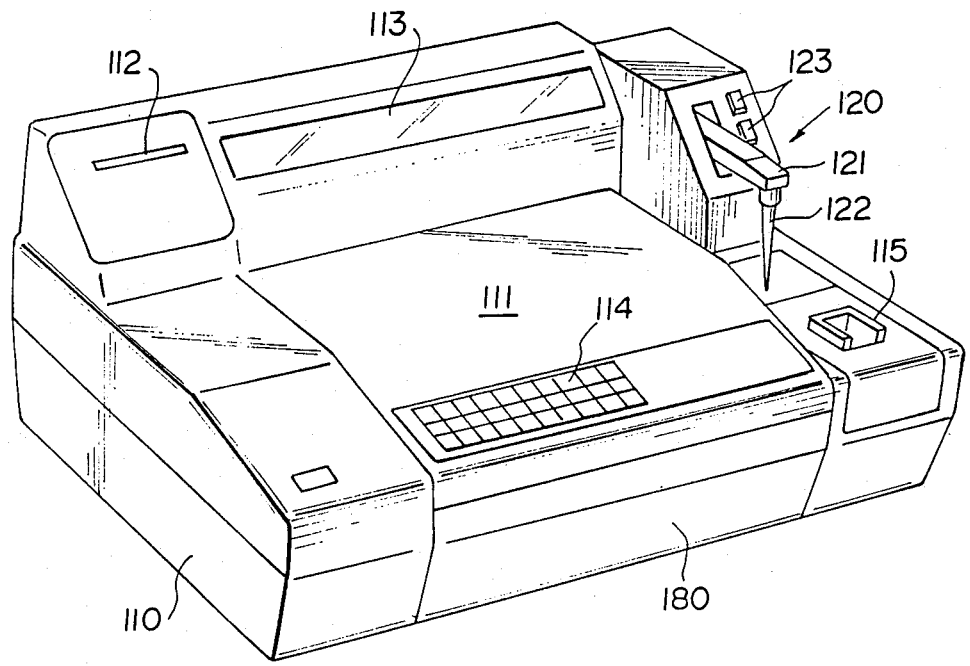
FIG. 7 is a perspective view showing another embodiment of the chemical analysis apparatus in accordance with the present invention.

In the embodiment of FIG. 7, an incubator, a slide conveyance means, a slide feed-in means and the like are disposed in a main body 110, and covered with a cover 111. An insertion opening 112 for insertion of a magnetic disk for recording the measured values or the like, a display section 113 for displaying the measured values or the like, and an operating key section 114 for controlling the displaying or the like are disposed on the outer side of the chemical analysis apparatus. A slide guide 115 for holding an unused chemical analysis slide is disposed on the right side of the upper surface of the chemical analysis apparatus, and chemical analysis slides loaded from the exterior are held one by one or together in the stacked form by the slide guide 115. Or, a cartridge housing a plurality of the chemical analysis slides may be fitted to the slide guide 115. A sample applying means 120 for applying a predetermined sample solution onto the film 1b of the chemical analysis slide is disposed at the rear of the slide guide 115. The sample applying means 120 is composed of a sample applying arm 121 projecting forwardly and vertically rotatable around its rear end, a sample applying pipette 122 extending downwardly from the front end of the sample applying arm 121, and operating push-buttons 123, 123 for controlling the vertical movement of the sample applying arm 121 and the drawing-in and discharging of the sample solution in the sample applying pipette 122. In the course of application by the sample applying means 120, the sample applying arm 121 is rotated up to move the sample applying pipette 122 up by the operation of the operating buttons 123, 123, a sample solution contained in a vessel is made to contact the lower end of the sample applying pipette 122, and a predetermined amount of the sample solution is drown into the sample applying pipette 122. Then, the sample applying arm 121 is rotated down, and the predetermined amount of the sample solution is applied from the sample applying pipette 122 onto the film 1b of the chemical analysis slide disposed below the sample applying pipette 122.

Figure 8:
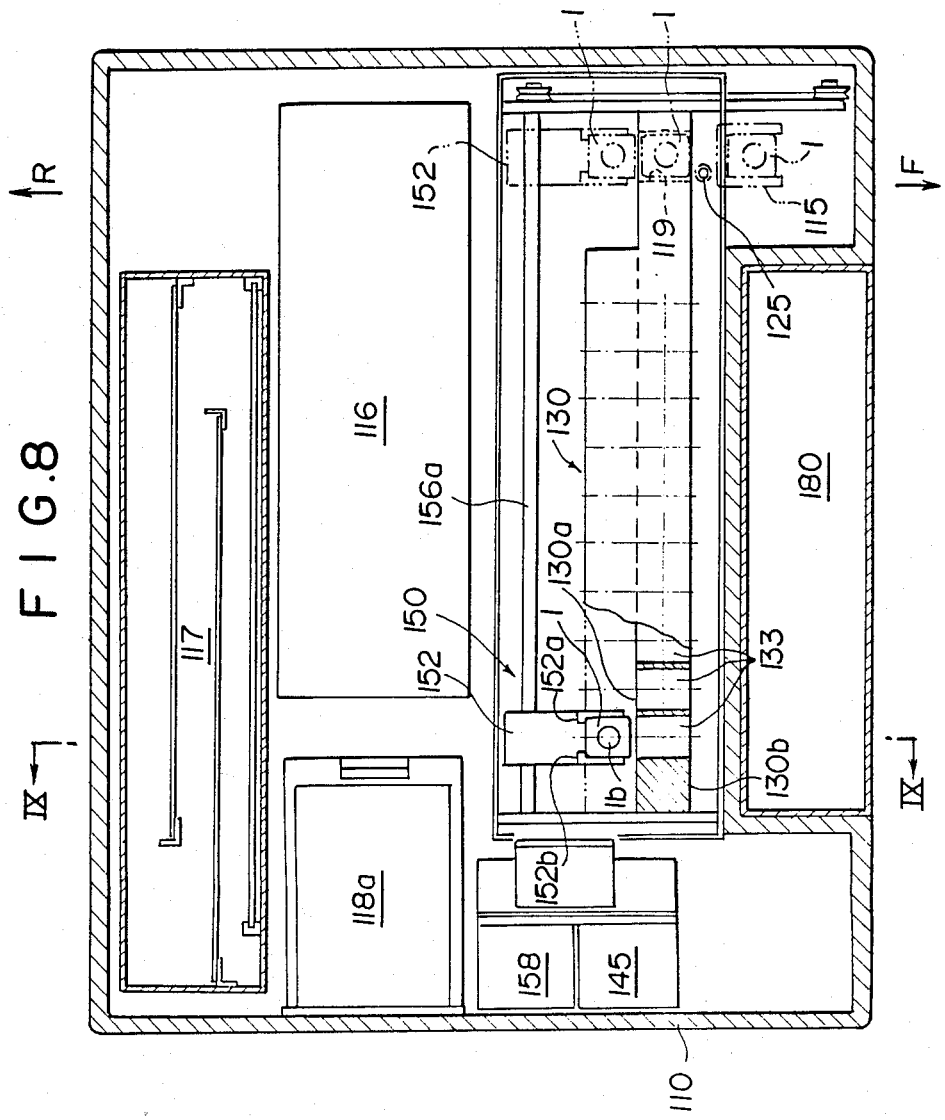
FIG. 8 is a plan view showing the internal configuration of the embodiment of FIG. 7.
Figure 9:
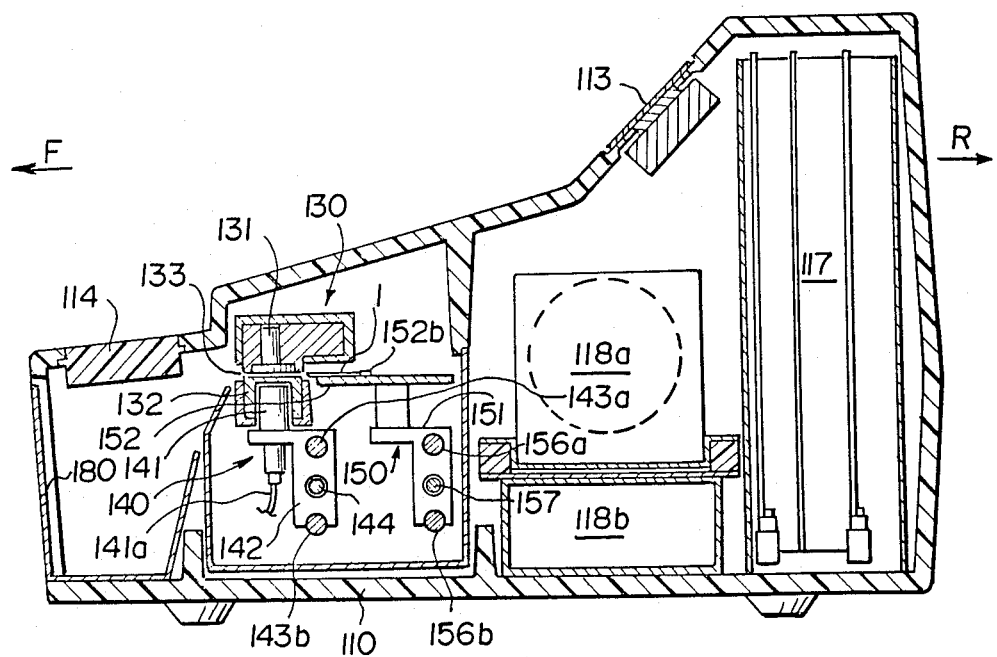
FIG. 9 is a sectional view taken along line IX—IX of FIG. 8.

FIG. 8 is a plan view showing the internal configuration of the embodiment of FIG. 7, and FIG. 9 is a sectional view taken along line IX—IX of FIG. 8. The internal configuration of the embodiment of FIG. 7 will hereinbelow be described with reference to FIGS. 8 and 9. An incubator 130 for incubating the chemical analysis slide provided with the sample solution by the sample applying means 120, an optical reading means 140 for optically detecting the extent of a color reaction in the incubated chemical analysis slide, and a conveyance and feed-in means 150 for conveying the chemical analysis slide to the incubator 130 and feeding it into one of housing compartments 133, 133, . . . of the incubator 130 are disposed inside of the chemical analysis apparatus. This embodiment is also provided with an electric power source 116, a printed circuit board 117 for a control circuit, a light source 118a for the optical reading means 140, and a magnetic disk drive mechanism 118b. In the description below, the direction as indicated by the arrow F is referred to as the forward direction or the front side, the direction as indicated by the arrow R is referred to as the backward direction or the rear side, and the right side and the left side are referred to with respect to FIG. 8.

The incubator 130 extends in the rightward-leftward direction, and a plurality of the housing compartments 133, 133, . . . are disposed side by side in the rightward-leftward direction in the incubator 130. The housing compartments 133, 133, . . . are provided with inlet openings and outlet openings. The inlet openings are disposed side by side in the rightward-leftward direction along a lower rear and face 130a of the incubator 130, and the outlet openings are disposed side by side in the rightward-leftward direction along a front end face 130b of the incubator 130. Therefore, the chemical analysis slide 1 is fed into the housing compartment 133 from its inlet opening, and ejected from its outlet opening. The chemical analysis slide 1 ejected from the outlet opening is discharged into an ejection box 180 disposed in front of the incubator 130. Also, the housing compartment 133 is provided with a lower member 132 for supporting the chemical analysis slide 1 thereon, and an upper member 131 for holding the chemical analysis slide 1, which is supported on the lower member 132, from above. The chemical analysis slide 1 is incubated by the upper member 131 and the lower member 132.

The optical reading means 140 is disposed under the incubator 130 and is composed of an upper guide rod 143a and a lower guide rod 143b which extend in the rightward-leftward direction a drive rod 144 having threads on the outer circumference and extending in the rightward-leftward direction between the guide rods 143a and 143b, a drive motor 145 for rotating the drive rod 144, a supporting base 142 slideable on the guide rods 143a and 143b and engaged by threads with the drive rod 144, and a read-out head 141 mounted on the supporting base 142. The supporting base 142 is moveable together with the read-out head 141 in the rightward-leftward direction on the guide rods 143a and 143b as the drive rod 144 is rotated by the drive motor 145. The read-out head 141 stands facing the lower surface of the lower member 132 of the incubator 130, emits measuring light to the film 1b of the chemical analysis slide 1, which is housed in the housing compartment 133, via a measuring hole formed in the lower member 132 at each housing compartment 133, and measures the reflection optical density of the film 1b. For this purpose, the read-out head 141 moving together with the supporting base 142 in the rightward-leftward direction can be moved to the position facing the measuring hole of each housing compartment 133 and can measure the extent of the color reaction in the chemical analysis slide 1 housed in an arbitrary housing compartment 133. The measuring light is emitted by the light source 118a and guided to the read-out head 141 through an optical fiber 141a. The read-out head 141 can be moved in the rightward-leftward direction to the position facing each housing compartment 133 and to the position facing the lower surface of a conveyance compartment 119 through which the chemical analysis slide 1 conveyed from the slide guide 115 to the conveyance and feed-in means 150 passes, thereby conducting fog measurement at the conveyance compartment 119.

The conveyance and feed-in means 150 is disposed at the rear of the incubator 130 for conveying the chemical analysis slide 1 with the sample solution applied thereon by the sample applying means 120 to the position facing the inlet opening of each housing compartment 133 and feeding the chemical analysis slide 1 into the housing compartment 133. The conveyance and feed-in means 150 is composed of an upper guide rod 156a and a lower guide rod 156b which extend in the rightward-leftward direction, a conveyance rod 157 having threads on the outer circumference and extending in the rightward-leftward direction between the guide rods 156a and 156b, a conveyance motor 158 for rotating the conveyance rod 157, a conveyance base 151 slideable on the guide rods 156a and 156b and engaged by threads with the conveyance rod 157, and a slide receiving base 152 secured to the conveyance base 151. The conveyance base 151 is moveable together with the slide receiving base 152 in the rightward-leftward direction on the guide rods 156a and 156b as the conveyance rod 157 is rotated by the conveyance motor 158. In FIG. 8, the conveyance base 151 is moveable between the position as indicated by the chain line at the rear of the slide guide 115 and the position as indicated by the solid line facing the housing compartment 133 at the left end of the incubator 130. The slide receiving base 152 is disposed so that its front end faces the inlet opening of each housing compartment 133 in the course of movement in the rightward-leftward direction. A pair of guides 152a and 152b for holding the chemical analysis slide 1 is formed on the front upper surface of the slide receiving base 152. The slide receiving base 152 is moveable forwardly and backwardly with respect to the conveyance base 151 like the supporting plate 41 shown in FIG. 4A. Therefore, when the slide receiving base 152 is moved to the position at the rear of the slide guide 115 as indicated by the chain line in FIG. 8, the chemical analysis slide 1 held at the slide guide 115 is conveyed onto the slide receiving base 152 by a pushing lever, a conveyor belt or the like, and placed on the slide receiving base 152 by being guided by the guides 152a and 152b. In the course of the conveyance, the bar code of the chemical analysis slide 1 is read by a bar code sensor 125. Also, when the chemical analysis slide 1 is made to pass through the conveyance compartment 119 disposed side by side with the housing compartments 133, 133, . . . on the lateral side on the same plane as the housing compartments 133, 133, . . . , the reflection optical density (fog density) of the chemical analysis slide 1 prior to the sample solution being applied thereto is measured by the read-out head 141 moved to the position facing the lower surface of the conveyance compartment 119. On the chemical analysis slide 1 thus conveyed and placed on the slide receiving base 152 is applied the sample solution, onto the reagent layer, by the sample applying means 120 at that position. Then the slide receiving base 152 is moved together with the conveyance base 151 leftwardly, and the chemical analysis slide 1 placed on the slide receiving base 152 is conveyed up to the position facing the inlet opening of the predetermined one of the housing compartments 133, 133, . . . .

Thereafter, the slide receiving base 152 is moved forwardly on the conveyance base 151 to feed the chemical analysis slide 1 into the housing compartment 133. The feeding operations are the same as mentioned with reference to FIGS. 6A to 6D.

We claim:

1. A chemical analysis apparatus comprising:
   (i) a slide loading section for holding at least one chemical analysis slide,
   (ii) a sample applying section for applying a predetermined amount of a sample material to said at least one chemical analysis slide,
   (iii) an incubator provided with a plurality of stationary housing compartments, each of said housing compartments being provided for separately housing a respective one of a plurality of chemical analysis slides, said housing compartments being placed side by side in a transverse direction in the same plane of said incubator,
   (iv) a read-out head slideable in said transverse direction and disposed for facing a chemical analysis slide when it is housed in one of said plurality of said housing compartments via a respective read-out opening (21a) formed in each of said housing compartments, thereby emitting light to said chemical analysis slide and measuring reflection optical density of said chemical analysis slide, and
   (v) a conveyance and feed-in means for conveying a respective one of said chemical analysis slides from said slide loading section to said sample applying section, conveying the respective one of said chemical analysis slide from said sample applying section to a position facing an inlet opening of a respective one of said housing compartments, and then feeding said respective chemical analysis slide into the respective one of said housing compartments through the inlet opening thereof.

2. An apparatus as defined in claim 1 wherein said sample applying section applies a predetermined amount of the sample material on an upper surface of said chemical analysis slide, and said read-out head faces a lower surface of said chemical analysis slide and measures the reflection optical density.

3. A chemical analysis apparatus comprising:
   (i) a slide loading section for holding at least one chemical analysis slide,
   (ii) a sample applying section for applying a predetermined amount of a sample material to said at least one chemical analysis slide,
   (iii) an incubator provided with a plurality of stationary housing compartments each of which is provided for separately housing a respective one of a plurality of chemical analysis slides, said housing compartments being placed side by side in a transverse direction in the same plane of said incubator,
   (iv) a read-out head slideable in said transverse direction and disposed for facing the respective one of said chemical analysis slides when it is housed in the respective one of said plurality of the housing compartments via a read-out opening formed in each of said housing compartments, thereby emitting light to the respective one of said chemical analysis slides and measuring reflection optical density thereof,
   (v) a conveyance and feed-in means for conveying each respective one of said chemical analysis slides from said slide loading section to said sample applying section, conveying each respective one of said chemical analysis slides from said sample applying section to a position facing an inlet opening of a respective one of said housing compartments, and then feeding each respective one of said chemical analysis slides into the respective one of said housing compartments through the inlet opening thereof, wherein a fog measuring section for measuring the reflection optical density of each of said chemical analysis slides before each of said chemical analysis slides is provided with said sample material is disposed on the lateral side of said incubator in said transverse direction, and wherein means for moving said read-out head in said transverse direction to face said fog measuring section is provided, and said chemical analysis slides conveyed by said conveyance and feed-in means from said slide loading section to said sample applying section are passed through said fog measuring section, whereby fog measurement is conducted by said read-out head at said fog measuring section.

4. An apparatus as defined in claim 3 wherein said sample applying section applies a predetermined amount of the sample material to an upper surface of said chemical analysis slide, and said read-out head faces a lower surface of said chemical analysis slide and measures the reflection optical density.

5. A chemical analysis apparatus comprising:
   (i) a sample applying section for applying a predetermined amount of a sample material to a reagent layer of a chemical analysis slide provided with at least one reagent layer,
   (ii) a first incubator provided with a plurality of stationary first housing compartments each of which is provided for separately housing a respective one of a plurality of chemical analysis slides, said housing compartments being placed side by side in a transverse direction in the same plane of said first incubator,
   (iii) a second incubator disposed on the lateral side of said first incubator in said transverse direction and provided with at least one second housing compartment for housing at least one chemical analysis slide and standing side by side with said plurality of stationary first housing compartments in said transverse direction in the same plane as said plurality of stationary first housing compartments,
   (iv) a read-out head slideable in said transverse direction and disposed for facing said at least one reagent layer of a respective one of said chemical analysis slides housed in a respective one of said plurality of stationary first housing compartments via a respective read-out opening formed in each of said plurality of stationary first housing compartments, thereby emitting light to said at least one reagent layer and measuring reflection optical density of said at least one reagent layer thereof, and
   (v) a conveyance and feed-in means, disposed slideably in said transverse direction to face inlet openings of said plurality of stationary first housing compartments and said at least one second housing compartment, for conveying said plurality of chemical analysis slides one by one to said sample applying section, conveying each respective one of said plurality of chemical analysis slides one by one from said sample applying section to a position facing an inlet opening of a respective one of said plurality of stationary first housing compartments or an inlet opening of said at least one second housing compartment, and then feeding the respective one of said plurality of chemical analysis slides into the respective one of said plurality of stationary first housing compartments or said at least one second housing compartment through the inlet opening thereof.

6. An apparatus as defined in claim 5 wherein a fog measuring section (16) for measuring the reflection optical density of a chemical analysis slide before it is provided with said sample material is disposed on the lateral side of said first incubator in said transverse direction, said read-out head is slideable in said transverse direction to face said fog measuring section, and said chemical analysis slide conveyed by said conveyance and feed-in means to said sample applying section is passed through said fog measuring section, whereby fog measurement is conducted by said read-out head at said fog measuring section.

7. An apparatus as defined in claim 5 or 6 wherein said sample applying section applies a predetermined amount of the sample material to an upper surface of said chemical analysis slide, and said read-out head stands facing a lower surface of said chemical analysis slide and measures the reflection optical density.

8. A chemical analysis apparatus comprising:
(i) an incubator provided with a plurality of stationary housing compartments each of which is provided for separately housing a respective one of a plurality of chemical analysis slides and maintaining said chemical analysis slides at a predetermined temperature, each of said slides having a reagent layer with a sample material applied thereto,
(ii) a movable read-out head for movement to respective positions for facing each said reagent layer of each of said chemical analysis slides when the chemical analysis slides are housed in respective ones of said housing compartments via respective read-out openings formed in said housing compartments, emitting light to each said reagent layer, and measuring reflection optical density of each said reagent layer, and
(iii) a slide feed-in and ejection means for each of said housing compartments for ejecting a chemical analysis slide when it is housed in one of said housing compartments out of said housing compartment and feeding another chemical analysis slide into said housing compartment,
wherein each of said housing compartments of said incubator is provided with a supporting member for supporting one surface of a chemical analysis slide when said chemical analysis slide is in said housing compartment and said supporting member having a read-out opening, and a pushing member contacting the other surface of said chemical analysis slide and urged toward said one surface of said chemical analysis slide, thereby grasping said chemical analysis slide between said pushing member and said supporting member, said housing compartment having an inlet opening provided with a stopper member for allowing a chemical analysis slide to enter said housing compartment through said inlet opening and preventing a chemical analysis slide when it is in said housing compartment from coming out of said housing compartment, and each said slide-in and ejection means comprising:
(a) a holding portion capable of being inserted into said housing compartment and supporting a second of said plurality of chemical analysis slides thereon,
(b) wedge-like insert portion disposed at a front end of said holding portion for releasing the grasping of a chemical analysis slide when it is in said housing compartment by said pushing member by engaging and lifting said pushing member to a release position where its grasp is released when said wedge-like insert portion is inserted into said housing compartment, and step-like portions, formed on said slide feed-in and ejection means at opposing lateral edges of the holding portion projecting above said holding portion, for maintaining said pushing member in said release position during feeding in of said second of said plurality of chemical analysis slides,
(c) a slide ejecting protrusion disposed on the front end of said holding portion, said protrusion having a pushing face for contacting the rear end of a chemical analysis slide when said chemical analysis slide is in said housing compartment and pushing said chemical analysis slide toward an outlet opening disposed on the side opposite to said inlet opening, thereby ejecting said chemical analysis slide, and
(d) an engagement means for making second of said plurality of chemical analysis slides engage with said stopper member when said second of said plurality of chemical analysis slides is supported on said holding portion and is positioned inside said housing compartment.

9. An apparatus as defined in claim 8 wherein said stopper member disposed at said inlet opening of said housing compartment is a leaf spring, and said engagement means of said slide feed-in and ejection means comprises a recess formed at a rear end of said holding portion for engaging with a leading end of said leaf spring.

* * * * *